(12) United States Patent
Oosterbroek et al.

(10) Patent No.: US 9,442,109 B2
(45) Date of Patent: Sep. 13, 2016

(54) CENTRIFUGAL FORCE BASED MICROFLUIDIC SYSTEM AND METHOD FOR THE AUTOMATED ANALYSIS OF SAMPLES

(75) Inventors: Rijk Edwin Oosterbroek, Cham (CH); Mario Curcio, Sins (CH); Stephan Korner, Cham (CH); Brigitte Niederberger, Thalwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1497 days.

(21) Appl. No.: 12/781,473

(22) Filed: May 17, 2010

(65) Prior Publication Data
US 2011/0124128 A1 May 26, 2011

(30) Foreign Application Priority Data

May 18, 2009 (EP) .................... 09160558

(51) Int. Cl.
*C12M 1/00* (2006.01)
*G01N 33/543* (2006.01)
*B01L 3/00* (2006.01)

(52) U.S. Cl.
CPC ... *G01N 33/54326* (2013.01); *B01L 3/502761* (2013.01); *B01L 2200/0668* (2013.01); *B01L 2300/0803* (2013.01); *B01L 2400/043* (2013.01); *B01L 2400/0409* (2013.01)

(58) Field of Classification Search
CPC ................. B01L 3/502761; B01L 2200/0668; B01L 2300/0803; B01L 2400/0409; B01L 2400/043; G01N 33/54326
USPC ....................... 435/289.1; 436/526
See application file for complete search history.

(56) References Cited

U.S. PATENT DOCUMENTS

| | | | |
|---|---|---|---|
| 7,015,780 B2 * | 3/2006 | Bernstein et al. | ............ 335/302 |
| 2006/0011552 A1 | 1/2006 | Utsunomiya | |
| 2006/0068409 A1 | 3/2006 | Phan et al. | |
| 2008/0035579 A1 | 2/2008 | Lee et al. | |
| 2008/0073546 A1 * | 3/2008 | Andersson et al. | ... 250/396 ML |
| 2009/0023610 A1 * | 1/2009 | Peytavi | ......................... 506/39 |
| 2009/0035847 A1 * | 2/2009 | Cho et al. | .................. 435/289.1 |

FOREIGN PATENT DOCUMENTS

| | | |
|---|---|---|
| EP | 1 897 617 A1 | 3/2008 |
| JP | 2006010529 A | 1/2006 |
| JP | 20080161649 A | 3/2008 |
| JP | 2008539419 A | 11/2008 |
| WO | 2007/106013 A1 | 9/2007 |

OTHER PUBLICATIONS

European Search Report, Appln. No. EP 09 16 0558, filed May 19, 2009, report completed Sep. 17, 2009, pp. 1-6.

* cited by examiner

*Primary Examiner* — Mark Shibuya
*Assistant Examiner* — Pensee Do
(74) *Attorney, Agent, or Firm* — Dinsmore & Shohl LLP

(57) ABSTRACT

Centrifugal force based microfluidic systems for the automated analysis of fluids involving the use of magnetically responsive particles and methods thereof are disclosed. A magnet is fixed to a supporting device of the system in correspondence to a retention zone of the system so as to rotate therewith and to generate a magnetic field which magnetically manipulates the magnetically responsive particles contained in a reaction chamber of the system.

20 Claims, 9 Drawing Sheets

CENTRIFUGAL FORCE BASED MICROFLUIDIC SYSTEM AND METHOD FOR THE AUTOMATED ANALYSIS OF SAMPLES

TECHNICAL FIELD

The present disclosure relates generally to the field of medical diagnostics and in particular, discloses various embodiments directed to a centrifugal force based microfluidic system and a method for the automated analysis of samples containing at least one analyte involving the use of magnetically responsive particles that are adapted to interact specifically with the analyte.

BACKGROUND

In medical diagnostics, a strong demand for the automated analysis of body fluids can be observed which is primarily due to the fact that there is an ongoing increase in the number of clinical analyses. Due to low sample consumption, fast analysis times and high sample throughput, in recent years, many efforts have been made to develop microfluidic systems, among these centrifugal force based microfluidic systems, for the automated analysis of samples having minute volumes as low as micro-liters.

In general, centrifugal-force based microfluidic systems include a plurality of microfluidic structures for receiving the samples. Each microfluidic structure enables an individual sample to be transferred from an inlet zone to a reaction chamber for enabling a reaction of the analyte and detection of a reaction product to determine presence and optionally concentration of the analyte.

SUMMARY

It is against the above background that various embodiments provide improved centrifugal force based microfluidic systems and methods for the automated analysis of samples.

In one embodiment, a centrifugal force based microfluidic system for the automated analysis of samples containing at least one analyte involving the use of magnetically responsive particles which interact with said analyte is disclosed. The system comprises: at least one rotatable supporting device; at least one microfluidic device fixed to said supporting device so as to rotate therewith and provided with at least one microfluidic structure having at least one inlet zone, at least one reaction chamber which receives one of said samples and which is in fluid communication with said at least one inlet zone comprising at least one retention zone which retains said magnetically responsive particles; and at least one magnet fixed to said supporting device in correspondence to said at least one retention zone so as to rotate therewith and to generate a magnetic field which magnetically manipulates said magnetically responsive particles contained in said at least one reaction chamber.

In another embodiment, a method for the automated analysis of samples containing at least one analyte involving the use of magnetically responsive particles which interact specifically with said analyte is disclosed. The method comprises: providing a microfluidic system comprising a rotatable sup-porting device and at least one microfluidic device fixed to said supporting device so as to rotate therewith, said microfluidic device having at least one microfluidic structure comprising at least one reaction chamber including at least one retention zone for retaining said magnetically responsive particles; introducing one of said samples into said reaction chamber; introducing said magnetically responsive particles into said reaction chamber; and applying a magnetic field to said retention zone to magnetically manipulate said magnetically responsive particles.

These and other features and advantages of the various embodiments will appear more fully from the following description, and the accompanying drawings, which are incorporated in and constitute a part of the specification.

REFERENCE LIST

Figure 1:
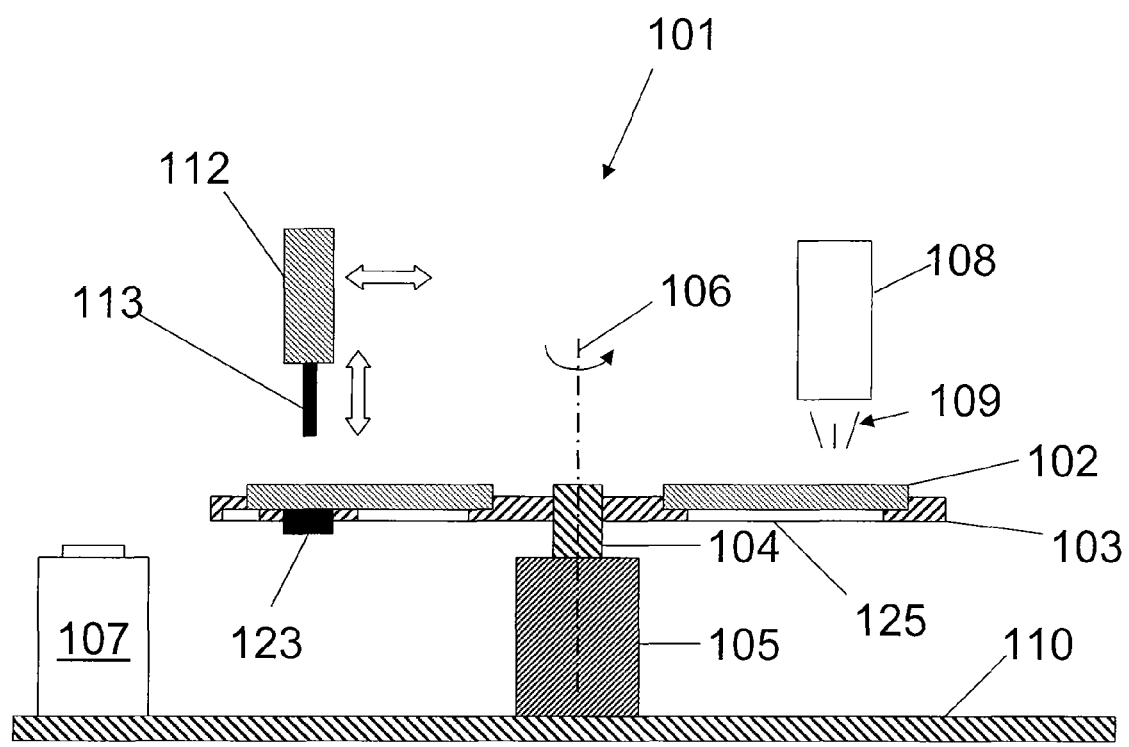
FIG. 1 depicts a schematic sectional view of an exemplary embodiment of a microfluidic system for the automated analysis of samples.

101 System
102 Chip
103 Platform
104 Shaft
105 Motor
106 Rotational axis
107 Reservoir
108 Detecting unit
109 Light
110 Base plate
111 Cavity
112 Pipetting unit
113 Pipetting tip
114 Microfluidic structure
115 Sample inlet zone
116 Sample conduit
117 Particle inlet zone
118 Particle conduit
119 Reaction chamber
120 Retention zone
121 Waste zone
122 Waste conduit
123 Magnet
124 Recess
125 Opening
126 Particles 127 Cover foil
201 System
202 Chip
203 Platform
204 Shaft
205 Motor
206 Rotational axis
207 Reservoir
208 Detecting unit
209 Light
210 Base plate
211 Carrier
212 Pipetting unit
213 Pipetting tip
214 Microfluidic structure
215 Sample inlet zone
216 Sample conduit
217 Particle inlet zone
218 Particle conduit
219 First reaction chamber
220 First retention zone
221 Waste zone
222 Waste conduit
223 Second reaction chamber
224 Second retention zone
225 Inter-chamber conduit
226 First magnet
227 Second magnet
228 Particles
229 Guiding face
230 Third magnet

DETAILED DESCRIPTION

According to an embodiment, a centrifugal force based microfluidic system for the automated analysis of samples containing at least one analyte involving the use of magnetically responsive particles, adapted to interact specifically with the analyte, is disclosed. The centrifugal-force based microfluidic system may be used in (bio-) chemistry including in-vitro diagnostics and is adapted to carry out various assays typically comprising mixing between samples and reagents as well as detecting the result of those reactions. For example, the system may be used for diagnostic assays, such as clinical chemistry assays and immunoassays. Typical diagnostic assays include, for example, and not to be limited thereto, the qualitative and/or quantitative analysis of analytes such as albumin, ALP (alkaline phosphatase), ALT (alanine aminotransferase), ammonia, amylase, aspartat, aminotransferase, bicarbonate, bilirubin, calcium, cardiac markers, cholesterol, creatinine kinase, D-dimer, ethanol, g-glutamyltransferase, glucose, HBA1c (hemoglobin A1c), HDL-cholesterol, iron, lactate, lactate dehydrogenase, LDL-cholesterol, lipase, magnesium, phosphorus inorganic, potassium, sodium, total protein, triglycerides, UREA, and uric acid.

According to an embodiment, samples can be liquid fluids in which one or more analytes of interest can be potentially found. The system can perform on such liquid fluids one or more chemical assays such as, e.g., drug interaction screening, environmental analysis, identification of organic substances, etc. Samples in other embodiments can also be biological, such as body fluids, e.g., blood, serum, urine, milk, saliva, cerebrospinal fluid etc.

As used herein, the term "reagent" is used to indicate any liquid, e.g., a solvent or chemical solution which is to be mixed with a sample and/or other reagent in order, e.g., for a reaction to occur or to enable detection. A reagent can be, for example, another sample interacting with a first sample. A reagent can also be a diluting liquid such as, e.g., water. A reagent may comprise an organic solvent or a detergent. A reagent may also be a buffer. A reagent in the more strict sense of the term may be a liquid solution containing a reactant, typically a compound or agent capable, e.g., of binding to or transforming one or more analytes present in a sample. Examples of reactants are, for example, and not limited thereto, enzymes, enzyme substrates, conjugated dyes, protein-binding molecules, nucleic acid binding molecules, antibodies, chelating agents, promoters, inhibitors, epitopes, antigens, catalysts, etc. Optionally, dry reagents may be present in the analytical device and be dissolved by a sample, another reagent, or a diluting liquid.

According to an embodiment, reagents are heterogeneously mixed with samples and the assay is a heterogeneous assay. An example of a heterogeneous assay is a heterogeneous immunoassay in which some of the reactants, such as capturing antibodies, are immobilized on a solid support. According to an embodiment, the solid support comprises magnetically responsive particles. The magnetically responsive (i.e. magnetically attractable in one embodiment or magnetically repellable in another embodiment) particles may be embodied as magnetic beads or micro-spheres made of magnetic material provided with immobilized reactants, e.g., molecular binding elements such as antibodies adapted to specifically bind to at least one analyte contained in the sample.

Other examples of applications, and not limited thereto, are as follows: heterogeneous catalysis, wherein the magnetically responsive particles form or contain a catalytic surface; capturing and purification of nucleic acids via magnetically responsive beads, flakes or particles; capturing of other biological material such as cells or viruses by means of magnetically responsive particles; and chemical solid phase extraction.

In one embodiment, the microfluidic system includes at least one rotatable supporting device which, e.g., may have a disk-like shape that can be rotated around a rotational axis driven by means of an actuator such as an electric motor. In another embodiment, the microfluidic system includes at least one microfluidic device which, e.g., may have a disk-like shape that is fixed to the rotatable supporting device so to rotate therewith. The microfluidic device in one embodiment is provided with at least one or a plurality of microfluidic structures which, e.g., may be circumferentially arranged with respect to each other.

In another embodiment, the microfluidic device is removably fixed to the rotatable supporting device so that the microfluidic device can be mounted to the supporting device to co-rotate therewith for the automated analysis of samples and, otherwise, can be readily removed after sample analysis. Particularly, the microfluidic device may be embodied as disposable intended for single use only.

Each microfluidic structure in one embodiment includes at least one inlet zone for supplying at least one of said samples and/or magnetically responsive particles and/or reagents and/or other fluids such as washing buffer to at least one reaction chamber fluidically connected to the inlet zone. The reaction chamber comprises at least one retention zone adapted for the retention of the magnetically responsive particles. The retention zone may be embodied as a geometrically defined chamber-like or channel-like cavity, or as a free area comprised in the at least one reaction chamber, designed to retain at least partially and at least temporarily the magnetically responsive particles.

The reaction chamber may be used, e.g., for enabling binding of the analyte which may be contained in the sample to the magnetically responsive particles provided with molecular binding elements adapted to bind selectively to the analyte. The reaction chamber may be used, e.g., for labeling the particle-bound analytes with detectable labels such as fluorescence markers. The reaction chamber may be used, e.g., for washing out bound-free molecular detectable labels. The reaction chamber may be used, e.g., for receiving particles with bound labeled analytes for detection. Particularly, in one embodiment, the at least one retention zone of the reaction chamber may be used for the detection of the labeled particle-bound analytes.

In one embodiment, the microfluidic structure comprises at least one waste zone for receiving waste fluid fluidically connected to the at least one retention zone. The waste zone may include a waste reservoir which, e.g., by means of a siphon-like channel, is fluidically connected to the at least one reaction chamber.

The microfluidic structure as above-described enables the sample to be transferred from the inlet zone to the at least one reaction chamber and eventually at least partially to the waste zone by centrifugal force caused by rotating the microfluidic device. The inlet zone may be comprised of an inlet port and/or an inlet chamber fluidically connected to the at least one reaction chamber.

In another embodiment, the system further includes at least one magnet in correspondence to the at least one retention zone of the reaction chamber which being fixed to the rotatable supporting device co-rotates therewith for generating a magnetic field, adapted for magnetically manipulating the magnetically responsive particles contained in the reaction chamber, in particular for retaining magnetically responsive particles in the retention zone. The at least one magnet can be re-used for manipulating magnetically responsive particles in another microfluidic device rotationally fixed to the supporting device which advantageously allows for saving costs in producing the microfluidic device. Furthermore, mass (inertia) of the microfluidic device can be reduced. The at least one magnet may be, e.g., embodied as permanent magnet or electromagnet including a pole-shoe magnet, a switchable magnet or a toroidal magnet.

According to another embodiment, the magnetic field of the at least one magnet may be used for mixing and/or for washing and/or for retaining the magnetically responsive particles for detection.

According to still another embodiment, the microfluidic device of the microfluidic system is provided with at least one recess adapted for accommodating the at least one magnet so to reduce a distance between the retention zone and the magnet. By this measure, a magnetic force, e.g. pull force, for manipulating the magnetically responsive particles contained in the reaction chamber may advantageously be increased without a need to increase the magnetic strength of the magnet. A further noted advantage of such an embodiment, and not limited thereto, is an increased focusing effect resulting in an even, homogeneous and possibly smaller spot of the magnetically responsive particles which may be advantageous for detection purposes.

According to yet another embodiment, the microfluidic structure of the microfluidic system includes a first retention zone and a second retention zone which may be located within the same or another reaction chamber. The first retention zone may be located in a first reaction chamber and the second retention zone may be located in a second reaction chamber. Alternatively, the first and second retention zones may be located in one single reaction chamber. The second retention zone is in fluid communication with the first retention zone and adapted for retaining magnetically responsive particles. In this embodiment, the microfluidic system comprises at least one first magnet in correspondence to the first retention zone for generating a magnetic field adapted for retaining magnetically responsive particles in the first retention zone and at least one second magnet in correspondence to the second retention zone for generating a magnetic field adapted for retaining magnetically responsive particles in the second retention zone. The at least one second magnet is being fixed to the rotatable platform so that it (co-) rotates therewith. The first and second magnets may be, e.g., permanent magnets or electromagnets including pole-shoe magnets, switchable magnets or toroidal magnets.

According to another embodiment, the microfluidic structure of the microfluidic system includes a first retention zone and a second retention zone which is in fluid communication with the first retention zone. The system further comprises in another embodiment at least one first magnet fixed to the supporting device in correspondence to the at least one first retention zone so as to rotate therewith for generating a magnetic field adapted for retaining the magnetically responsive particles in the first retention zone. The system yet further comprises at least one second magnet fixed to the supporting device in correspondence to the at least one second retention zone so as to rotate therewith for generating a magnetic field adapted for retaining the magnetically responsive particles in the second retention zone. The system yet further comprises in another embodiment at least one third magnet separated from the supporting device so that the supporting device can be rotated with respect to the at least one third magnet. In one embodiment, the at least one third magnet is arranged in correspondence to the second retention zone for generating a magnetic field adapted for retaining magnetically responsive particles in the second retention zone. The at least one third magnet may be, e.g., a permanent magnet or electromagnet including a pole-shoe magnet, a switchable magnet or a toroidal magnet.

According to another embodiment, the microfluidic device of the microfluidic system is provided with at least one first recess adapted for accommodating the first magnet and at least one second recess adapted for accommodating the second magnet so as to reduce a distance between the first magnet and the first retention zone and between the second magnet and the second retention zone, respectively. By this measure, a magnetic force, e.g. pull force, for manipulating the magnetically responsive particles retained in the first and second retention zones, respectively, may advantageously be increased without a need to increase the magnetic strengths of the first and second magnets. A further advantage of this embodiment is an increased focusing effect resulting in an even, homogeneous and possibly smaller spot of the magnetically responsive particles which may be preferable for detection purposes.

According to still another embodiment, the microfluidic system further comprises at least one magnetic flux concentrator adapted for concentrating a magnetic flux of one more magnets selected from the group consisting of the at least one first magnet, the at least one second magnet and the at least one third magnet so as to increase magnetic interaction with the magnetically responsive particles in the first and/or second retention zones. Specifically, the at least one second magnet may be provided with a magnetic flux concentrator such as a pole shoe or any other concentrator geometry that concentrates the magnetic flux so that the magnetic field applied to the second retention zone is increased. A further noted advantage, and not limited thereto, of the above embodiment is an increased focusing effect resulting in an even, homogeneous and possibly smaller spot of the magnetically responsive particles which may be preferable for detection purposes.

According to another embodiment, the at least one second retention zone of the microfluidic system is provided with at least one guiding face adapted to locally accumulate (i.e. concentrate) the magnetically responsive particles within the second retention zone when magnetically manipulating the particles by the at least one second and/or third magnet. By this measure, an intensity of a detection signal for the detection of particle-bound analytes may advantageously be increased.

In one embodiment, the magnetic field of the at least one first (co-rotating) magnet, adapted for retaining the magnetically responsive particles in the first retention zone, may be used for moving the particles in the reaction chamber, e.g., by a combination of centrifugal force and magnetic force, in order to achieve more efficient mixing and/or washing during the assay or reaction. Likewise the magnetic field of the at least one second (co-rotating) magnet, adapted for retaining the magnetically responsive particles in the second retention zone, may be used for moving the magnetically responsive particles in the reaction chamber, e.g., by a combination of centrifugal force and magnetic force, in order to achieve more efficient mixing and/or washing during the assay or reaction.

Particularly, in another embodiment, the magnetic field of the at least one first magnet may be used for mixing and/or washing purposes and the magnetic field of the at least one second magnet may be used for retaining the magnetically responsive particles for detection.

In still another embodiment, the microfluidic system may further include a pipetting unit provided with at least one pipetting tip, adapted for transferring fluids with respect to the microfluidic structures.

In still other embodiments, the microfluidic system may yet further include a detecting unit, adapted for detecting particle-bound analytes contained in the retention zones. The detecting unit maybe embodied, e.g., as a fluorescence detector which includes a light source for the generation of light emitted towards the retention zones of the microfluidic structures and a fluorescence sensor for sensing of fluorescence light emitted from fluorescence markers made to be bound to the magnetically responsive particle-bound analytes.

In order to detect adequately particle-bound analytes, the particle-bound analytes are bound to detectable labels such as dyes, fluorescence or radioactive markers enabling selective detection of the particle-bound analytes.

In yet other embodiments, the microfluidic system may further include a controller for controlling the automated analysis of samples according to a predetermined process operation plan which, e.g., may be embodied as a programmable logic controller running a computer-readable program provided with instructions to perform operations in accordance with the process operation plan.

A suitable optical detection unit(s) in the microfluidic system include one or more light sources for emitting light and one or more light sensors such as, e.g., semiconductor light sensors known in the prior art. The optical detection unit may also comprise one or more suitable lenses and apertures in addition to the one or more light sources for generating light beams for illuminating the first and/or second retention zones. The term "light" as used herein is intended to encompass wavelength ranges that can be used by optical arrangements, e.g., ultraviolet and infrared light in addition to the visual range.

According to another embodiment, a method for the automated analysis of samples containing at least one analyte involving the use of magnetically responsive particles adapted to interact specifically with the analyte is disclosed.

In one embodiment, the method comprises providing a microfluidic system having a rotatable supporting device and at least one microfluidic device fixed to the supporting device so as to co-rotate therewith, wherein the microfluidic device has at least one microfluidic structure comprising at least one reaction chamber including at least one retention zone, which is adapted for retaining magnetically responsive particles. The method also includes introducing one of the samples into the reaction chamber; introducing the magnetically responsive particles into the reaction chamber; and applying a magnetic field to the retention zone, which magnetically manipulates the magnetically responsive particles.

In another embodiment, the method may further comprise introducing other reagents, e.g., containing molecular detectable labels or washing buffer into the at least one reaction chamber. In still another embodiment, the method may further comprise detecting particle-bound analytes retained in the at least one retention zone. Preferably, in one embodiment, the magnetically responsive particles are accumulated in the retention zone of the reaction chamber by the magnetic field at least when detection of the particles is performed.

In still other embodiments, the method may include, e.g., one or more of the following:

providing magnetically responsive particles in the at least one reaction chamber of the microfluidic structure by supplying the particles to an inlet zone fluidically connected to the reaction chamber and rotating the microfluidic device to thereby cause a centrifugal force sufficient to transfer the particles from the inlet zone into the reaction chamber;

providing the sample in the reaction chamber by supplying the sample to the same or a different inlet zone and rotating the microfluidic device to thereby cause a centrifugal force sufficient to transfer the sample into the reaction chamber in order to enable a reaction between the analyte which may be contained in the sample and analyte binding elements of the particles;

labeling of the particle-bound analytes with a detectable marker such as, e.g., a dye, or a fluorescence or radioactive marker;

removing unbound label molecules from the particle-bound analytes by washing;

applying a magnetic field to the at least one retention zone, e.g., by at least one magnet fixed to the supporting device;

moving the particle-bound analytes contained in the at least one reaction chamber, e.g., by a combination of centrifugal force and magnetic force, in order to achieve a more efficient mixing and/or washing during an assay or reaction;

moving the magnetically responsive particles radially back and forth by rotating the microfluidic device such that a centrifugal force is created that is sufficient for outbalancing the magnetic force of the magnetic field or by rotating the microfluidic device such that a centrifugal force is created that is outbalanced by the magnetic force of the magnetic fields; and/or detecting the particle-bound analytes retained in the retention zone.

The method in other embodiments may alternatively include one or more of the following:

providing magnetically responsive particles in the at least one reaction chamber of the microfluidic structure by supplying the particles to an inlet zone fluidically connected to a reaction chamber and rotating the microfluidic device to thereby cause a centrifugal force sufficient to transfer the particles from the inlet zone to the reaction chamber;

providing the sample in the reaction chamber by supplying the sample to the same or a different inlet zone and rotating the microfluidic device to thereby cause a centrifugal force sufficient to transfer the sample into the reaction chamber to enable a reaction between the analyte which may be contained in the sample and the analyte binding elements of the particles;

labeling of the particle-bound analytes with a detectable marker such as a dye or fluorescence or radioactive marker;

removing unbound label molecules from the particle-bound analytes by washing;

applying a first magnetic field to the reaction chamber in correspondence to a first retention zone, e.g., by a first magnet fixed to the supporting device;

moving the particle-bound analytes contained in the reaction chamber, e.g., by a combination of centrifugal force and magnetic force, in order to achieve more efficient mixing and/or washing during an assay or reaction;

transferring the particle-bound analytes to a second retention zone of the at least one reaction chamber;

applying a second magnetic field to the at least one reaction chamber in correspondence to the second retention zone, e.g., by a second magnet fixed to the supporting device; and/or detecting the particle-bound analytes retained in the at least one second retention zone.

In yet other embodiments, the method may include transferring the particle-bound analytes retained in the at least one first retention zone being part of a first reaction chamber into the at least one second retention zone being part of a second reaction chamber.

In still another embodiment, the method includes applying a magnetic field which is kept stationary with respect to the microfluidic system, and which accumulates and contains the magnetically responsive particles in the at least one retention zone. Such an embodiment may include performing a reciprocating rotary motion of the rotatable microfluidic device with respect to the magnetic field so to locally accumulate the magnetically responsive particles in the retention zone, followed by detecting the analytes bound to the accumulated particles. In another embodiment, an amplitude of the reciprocating rotary motion of the microfluidic device can be decreased from a maximum amplitude to a minimum amplitude, e.g., zero or thereabout, to thereby advantageously concentrate the particles around a centered position.

According to another embodiment, the method includes moving the magnetically responsive particles back and forth in radial direction by performing a rotational motion in which the microfluidic device is either rotated such that a centrifugal force is created that is sufficient for outbalancing a magnetic force acting on the particles or is rotated in another embodiment such that a centrifugal force is created that is outbalanced by the magnetic force.

The various embodiments of the present invention will now be described in detail below with reference to the accompanying drawings. With particular reference to FIGS. 1 to 5, an exemplary embodiment of a centrifugal force based microfluidic system 101 for the automated analysis of samples such as body fluids is explained. The microfluidic system 101 includes a disk-shaped microfluidic device, which in the following description is referred to as "chip 102", and which is supported by a disk-shaped rotatable supporting device, which in the following description is referred to as "platform 103". The platform 103 is concentrically arranged with respect to the chip 102 and coupled to a rotatably driven shaft 104 of an electric motor 105 so that the chip 102 and the platform 103 rotate around a common rotational axis 106. The chip 102 is removably fixed to the platform 103 by means of fixation elements (not shown), thereby making the chip 102 to co-rotate with the platform 103. Otherwise, the chip 102 can be easily removed from the platform 103 and, e.g., may be embodied as a disposable member to be disposed after use. While the chip 102 and the platform 103 both are shown to have a disk-like shape, the chip 102 and/or the platform 103 may have any other shape as desired dependent on the specific needs for the automated analysis of the samples.

Figure 2:
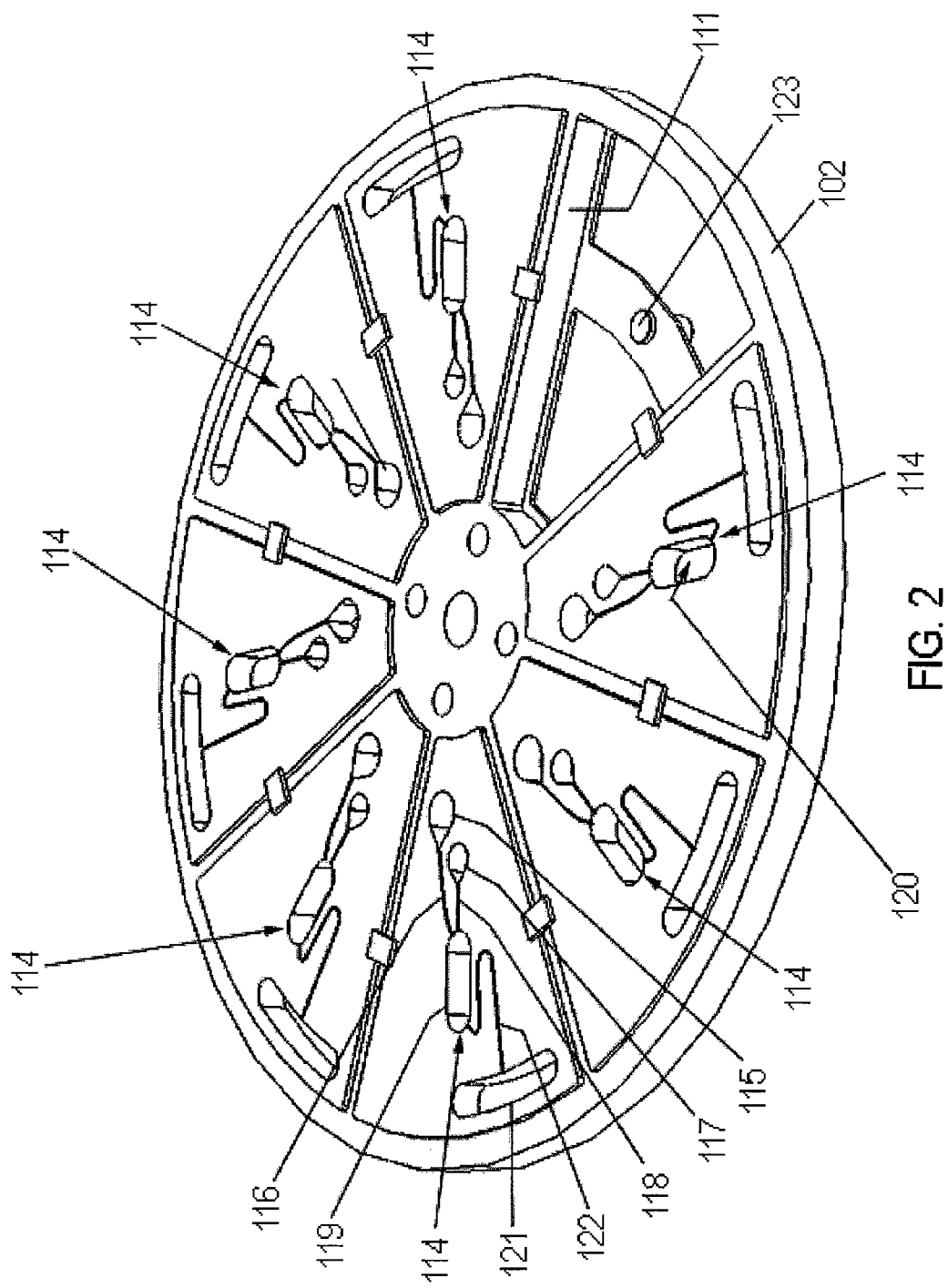
FIG. 2 depicts a schematic perspective view of the microfluidic system of FIG. 1.

As shown in FIG. 2, the chip 102 is provided with a plurality of microfluidic structures 114 adapted for receiving the samples and which are circumferentially arranged and equally-distanced with respect to each other. Stated more particularly, the chip 102 is provided with a plurality of segment-shaped cavities 111 accommodating the microfluidic structures 114. The cavities 111 may be regularly arranged in circumferential direction, e.g., covering the whole chip 102. While seven microfluidic structures 114 are shown for the purpose of illustration only, the chip 102 may be provided with any desired number of microfluidic structures 114 according to the specific needs for the automated analysis of samples.

Each microfluidic structure 114 includes a first inlet zone, which in the following description is referred to as "sample inlet zone 115" and which is comprised of an inlet port and a fluid reservoir (no further details provided for brevity). The sample inlet zone 115 is in fluid communication with a reaction chamber 119 by means of a micro-capillary fluid conduit, which in the following description is referred to as "sample conduit 116". The sample conduit 116 may be used, e.g., for supplying fluid samples and/or magnetically responsive particles and/or other reagents to the microfluidic structure 114. Each microfluidic structure 114 includes a second inlet zone, which in the following description is referred to as "particle inlet zone 117" and which is comprised of an inlet port and a fluid reservoir (no further details provided for brevity). The particle inlet zone 117 is in fluid communication with the reaction chamber 119 by means of another micro-capillary fluid conduit, which in the following description is referred to as "particle conduit 118". The particle inlet zone 117 may be used, e.g., for supplying fluid samples and/or magnetically responsive particles and/or other reagents to the microfluidic structure 114.

In each microfluidic structure 114, the reaction chamber 119 is in fluid communication with a waste zone 121, e.g., formed as a chamber, by means of another micro-capillary fluid conduit which, e.g., has a siphon-like structure. The micro-capillary fluid conduit in the following description is referred to as "waste conduit 122". In the microfluidic structure 114, fluid may be transferred from the sample inlet zone 115 to the waste zone 121 by means of a centrifugal force caused by rotating the platform 103 and in one embodiment if, e.g., a certain fluid volume in the reaction chamber 119 is exceeded. The waste zone 121, e.g., is adapted to receive excess fluid such as washing buffer used to wash out bound-free molecular (detectable) labels, while labeled magnetically responsive particle-bound analytes are retained in the reaction chamber 119 for detection.

In the microfluidic system 101, the platform 103 is provided with a plurality of platform-fixed magnets 123 which are arranged in such a manner that they are positioned below the reaction chambers 119 in correspondence to (i.e., in relation to) the retention zones 120 in order to retain the magnetically responsive particles within the reaction chambers 119. It is to be appreciated that since the magnets 123 are an integrated part of the platform 103, the magnets 123 co-rotate with the platform 103.

The microfluidic system 101 further includes a pipetting unit 112 provided with at least one pipetting tip 113 such as a metallic needle or a disposable tip, to transfer fluids from the fluid reservoirs 107 to the microfluidic structures 114. The reservoirs 107, one of which is illustrated in FIG. 1, can contain various fluids such as samples, suspensions of magnetically responsive particles, reagents, washing solutions and the like. The reservoirs 107 are placed on base plate 110. The pipetting unit 112 is operatively coupled to an automated positioning device (not shown) for transferring the pipetting tip 113 with respect to the reservoirs 107 and the chip 102. Since such pipetting unit 112 and positioning device are well-known to those of skill in the art they need not be further elucidated herein.

The microfluidic system 101 further includes a detecting unit 108 adapted for detecting labeled analytes contained in the reaction chambers 119. The detecting unit 108 may be, e.g., embodied as a fluorescence detector which includes a light source for the generation of light 109 that is emitted towards the retention zones 120 of the microfluidic structures 114, and a fluorescence sensor for sensing of fluorescence light that is emitted from fluorescence markers made to be bound to the particle-bound analytes contained in the reaction chambers 119. Since detection units, such as fluorescence detectors, are well-known to those of skill in the art, the detecting unit 108 need not be further elucidated herein.

The microfluidic system 101 yet further includes a controller (not shown) which, e.g., may be embodied as programmable logic controller running a computer-readable program provided with instructions to perform operations for the automated analysis of the samples. The controller receives information from the different components of the system 101, and also generates and transmits corresponding control signals for controlling the components. In order to perform the task, the controller is electrically connected to the system components which require control and/or provide information, which in one embodiment includes the motor 105, the pipetting unit 112 and the detecting unit 108.

Figure 4:
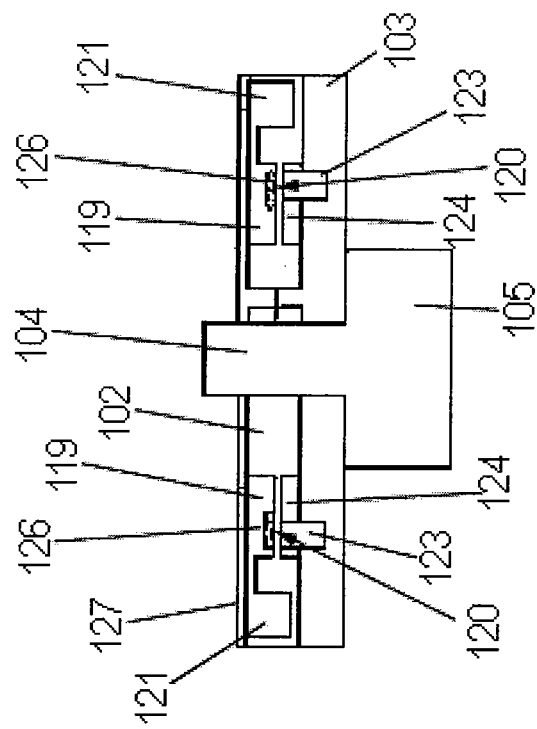
FIG. 4 depicts a schematic sectional view illustrating a variant of the microfluidic system of FIG. 1.
Figure 3:
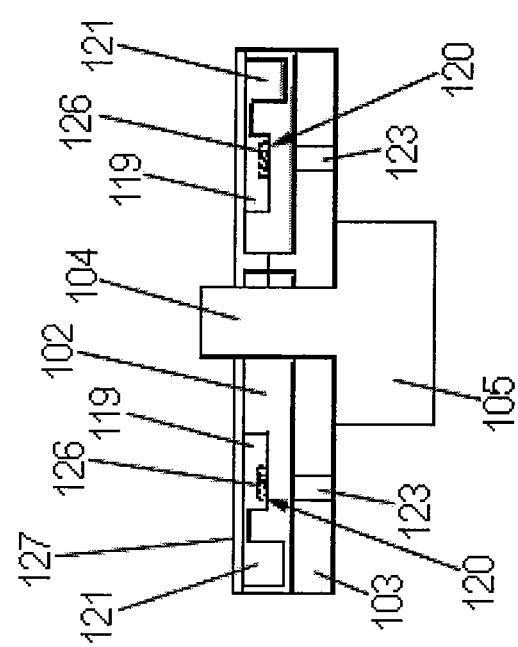
FIG. 3 depicts a schematic sectional view of the microfluidic system of FIG. 1 illustrating a detail thereof.

As illustrated in FIG. 1, the platform 103 may be provided with plural openings 125 in order to reduce its mass (inertia) and/or to provide access from beneath to the chip 102, e.g., for detecting analytes bound to the magnetically responsive particles 126 retained in the retention zones 120 of the reaction chambers 119 (FIGS. 3 and 4). Furthermore, as illustrated in FIGS. 3 and 4, the chip 102 is covered by an upper cover foil 127 for sealing the microfluidic structures 114. For optical reasons, this cover foil 127 advantageously is transparent. Analogously, at least a part of the chip 102 may be transparent.

With specific reference to FIG. 4 which illustrates a sectional view of a detailed portion of the microfluidic system 101 of FIG. 1, a variant thereof is explained. In this alternative embodiment, the chip 102 is provided with recesses 124 for accommodating the magnets 123 which are protruding towards the chip 102 to reduce a distance between the magnets 123 and the retention zones 120 of the reaction chambers 119.

Figure 5:
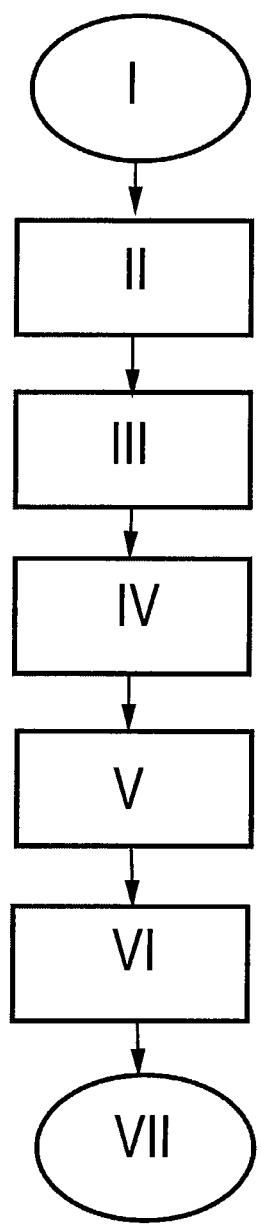
FIG. 5 depicts a flowchart illustrating a method for operating the microfluidic system of FIG. 1.

With specific reference to FIG. 5 illustrating a flowchart, an exemplary embodiment of a method for the automated analysis of samples using the microfluidic system 101 is explained.

I: The process starts.

II: Magnetically responsive particles 126 are provided in the reaction chambers 119. In one embodiment, the particles 126 are provided by using the pipetting tip 113 to transfer a suspension of magnetically responsive particles 126 from one of the fluid reservoirs 107, which contains the suspension, to each of the particle inlet zones 117, followed by rotating the platform 103 with a predetermined rotational speed to transfer predetermined volumes of the suspension from the particle inlet zones 117 through the particle conduits 118 to the reaction chambers 119 by means of centrifugal force. In one embodiment, the magnetically responsive particles 126 carry immobilized molecular binding elements attached to an outer surface thereof which can specifically bind to an analyte of which the presence and optionally concentration in the samples is to be tested. In another embodiment, the analyte may be attached to the outer surface of the magnetically responsive particles. When transferred to the reaction chambers 119, the magnets 123 magnetically attract the magnetically responsive particles 126 at the retention zones 120 within the reaction chambers 119.

III: Samples are provided in the reaction chambers 119 which contain an analyte that can specifically interact with and, e.g., bind to the particles 126. Such samples are provided in one embodiment by using the pipetting tip 113 to transfer the samples from another one of the reservoirs 107, which contain the samples, to each of the sample inlet zones 115, followed by rotating the platform 103 with a predetermined rotational speed in order to transfer the samples from the sample inlet zones 115 to the reaction chambers 119 by means of centrifugal force. Efficient mixing in the reaction chambers 119, which enables the analyte contained therein to specifically bind to the molecular binding elements of the magnetically responsive particles 126, may be achieved, e.g., by a combination of magnetic interaction and centrifugal force acting on the particles 126. Specifically, in one embodiment, the magnetically responsive particles 126 that are retained in the retention zones 120 can be moved back and forth in a radial direction by performing a rotational motion in which the chip 102 is either rotated such that a centrifugal force is created that is sufficient for outbalancing the magnetic force of the magnets 123, or in another embodiment is rotated such that a centrifugal force is created that is outbalanced by the magnetic force of the magnets 123.

IV: Labeling of the particle-bound analytes retained in the reaction chambers 119 is then performed. In one embodiment, the particle-bound analytes are labeled by use of the pipetting tip 113, wherein a fluid containing detectable molecular labels such as fluorescence markers adapted to specifically bind to the analytes, in this case to the particle-bound analytes, is transferred from another one of the reservoirs 107, which contains the labels, into each of the sample inlet zones 115 and/or the particle inlet zones 117 or another inlet zones (not shown). The transfer of the labels from one of the reservoirs 107 in one embodiment is then followed by rotating the platform 103 with a predetermined rotational speed in order to transfer the fluids from the sample inlet zones 115 towards the waste zones 121 passing through the reaction chambers 119 by means of centrifugal force. Supplying the label containing fluids to the reaction chambers 119 and, e.g., repeating the mixing process as previously described above enables the labels contained therein to specifically and efficiently bind to the particle-bound analytes.

V: Non-bound labels are then removed. In one embodiment, the non-bound labels are removed by use of the pipetting tip 113, wherein washing fluid is transferred from another one of the reservoirs 107, which contains the washing fluid, to each of the sample inlet zones 115. The transfer of the washing fluid in one embodiment is then followed by rotating the platform 103 with a predetermined rotational speed in order to transfer the washing fluid from the sample inlet zones 115 into the reaction chambers 119 by means of centrifugal force, thereby enabling the fluid surrounding the retained magnetically responsive particles 126 to be flushed away into the waste zones 121 and to be replaced by the washing fluid, thus removing the non-bound labels. Such washing may be repeated as often as necessary.

VI: The presence and optionally the concentration of the analyte in the samples are then determined. In one embodiment, an intensity of the labels, such as a fluorescence intensity of the labeled particle-bound analytes retained in the retention zones 120 of the reaction chambers 119, is measured by means of the detecting unit 108 and based on the result obtained, the presence and optionally the concentration of the analyte contained in the samples is determined.

VII: The process stops.

In the above described method, in other embodiments a different number of sample inlet zones 115 and/or particle inlet zones 117, e.g., only one single sample inlet zone 115 and/or only one single particle inlet zone 117 per microfluidic structure 114, could be used for all liquid additions. Moreover, in still other embodiments, different fluids could be introduced in a same or more sample inlet zones 115 and/or particle inlet zones 117 before being simultaneously transferred to the reaction chambers 119.

Figure 6:
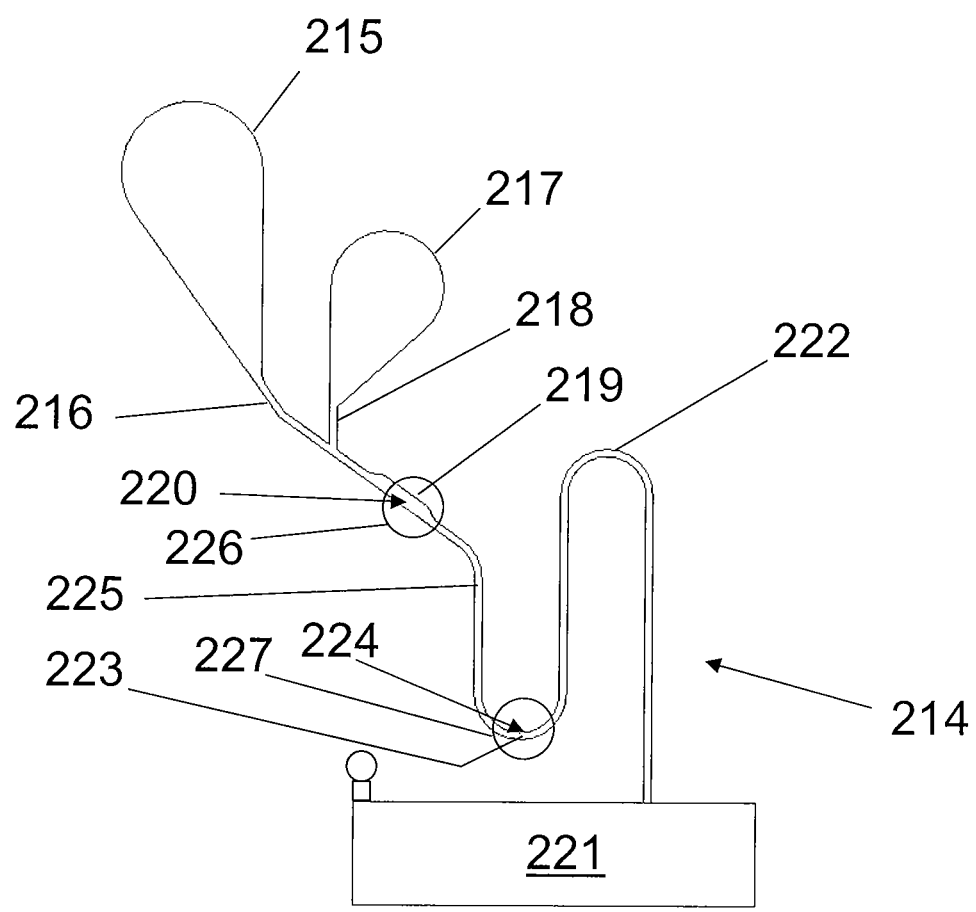
FIG. 6 depicts a schematic top view of an exemplary microfluidic structure of another exemplary embodiment of the microfluidic system as illustrated in FIG. 7.
Figure 7:
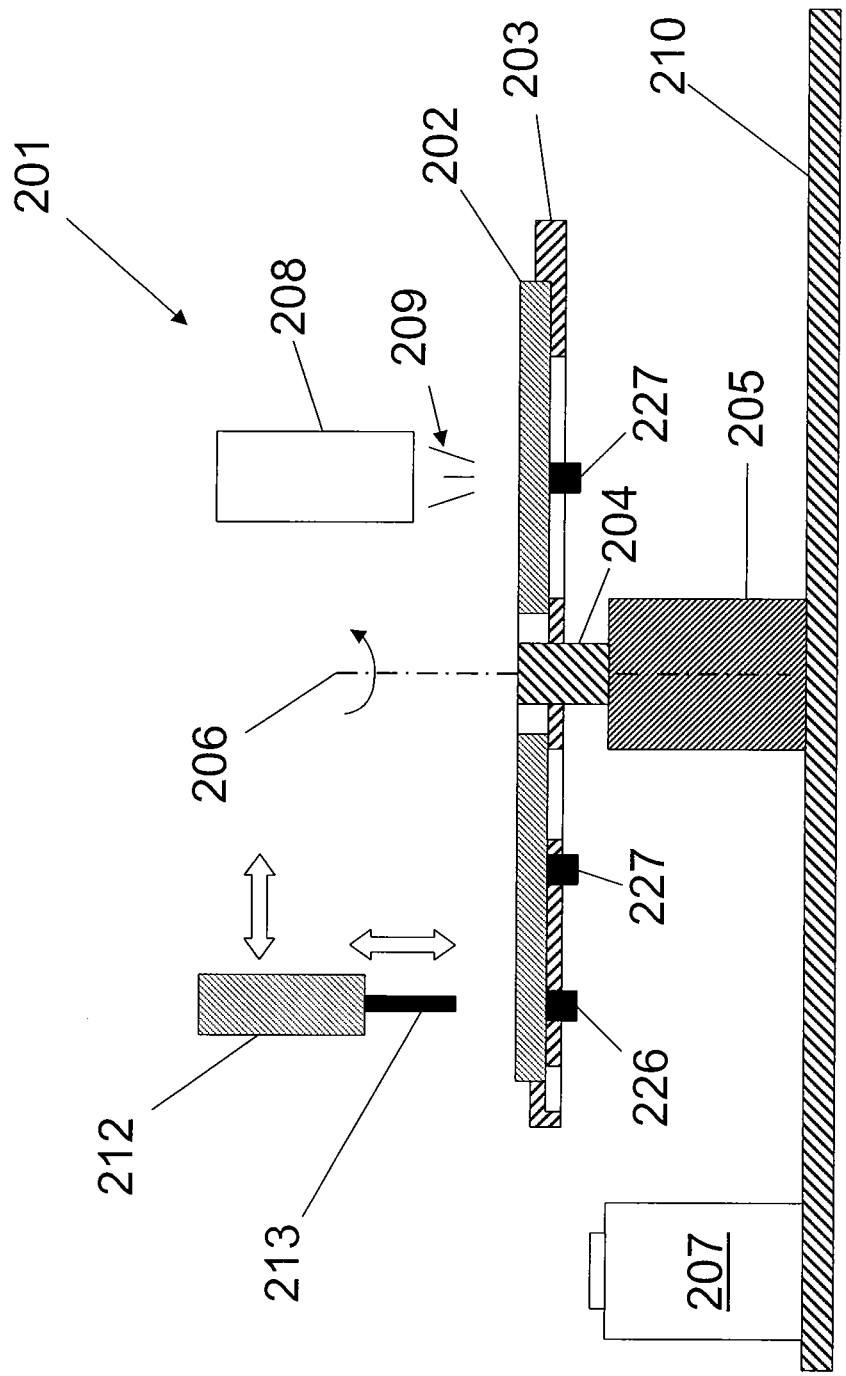
FIG. 7 depicts a schematic sectional view of another exemplary embodiment of the microfluidic system for the automated analysis of samples.
Figure 8:
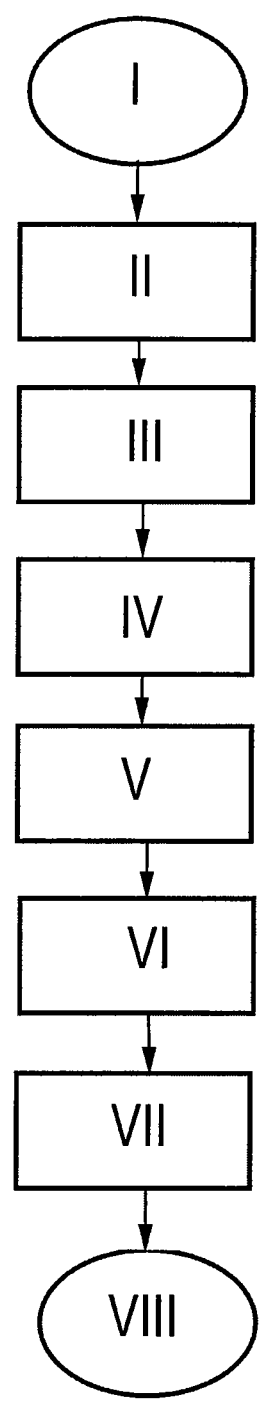
FIG. 8 depicts a flowchart illustrating a method for operating the microfluidic system of FIG. 7.

With particular reference to FIGS. 6 to 8, another exemplary embodiment of a centrifugal force based microfluidic system 201 for the automated analysis of samples is explained.

Similarly to the microfluidic system 101 of FIG. 1, the microfluidic system 201 includes a disk-shaped chip 202 which is supported by and removably fixed to a disk-shaped rotatable platform 203 which are concentrically arranged with respect to each other and coupled to a rotatably driven shaft 204 of electric motor 205 to rotate around a common rotational axis 206. The chip 202 is provided with a plurality of microfluidic structures 214.

Each microfluidic structure 214 includes a sample inlet zone 215 in fluid communication with a first reaction chamber 219 by means of a micro-capillary fluid conduit, which in the following description is referred to as "sample conduit 216". The sample inlet zone 215 may be used, e.g., for supplying fluid samples and/or magnetically responsive particles and/or other reagents to the microfluidic structure 214. The first reaction chamber 219 comprises a first retention zone 220 which may be, e.g., used for mixing magnetically responsive particles carrying molecular binding elements with samples containing at least one analyte for binding to the molecular binding elements as well as labeling and washing the labeled particle-bound analytes.

Each microfluidic structure 214 further includes a particle inlet zone 217 in fluid communication with the first reaction chamber 219 by means of a micro-capillary fluid conduit, which in the following description is referred to as "particle conduit 218". The particle inlet zone 217 may be used, e.g., for supplying fluid samples and/or magnetically responsive particles and/or other reagents to the microfluidic structure 214.

Each microfluidic structure 214 yet further includes a second reaction chamber 223 in fluid communication with the first reaction chamber 219 by means of a micro-capillary fluid conduit, which in the following description is referred to as "inter-chamber conduit 225". Otherwise, the second reaction chamber 223 is in fluid communication with a waste zone 221 by means of a waste conduit 222 which has a siphon-like structure. The second reaction chamber 223 comprises a second retention zone 224 which may be used, e.g., for detection of labeled particle-bound analytes after they have been transferred from the first reaction chamber 219 into the second reaction chamber 223.

The microfluidic system 201 further includes a pipetting unit 212 provided with at least one pipetting tip 213, adapted for transferring fluids from fluid reservoirs 207 to the microfluidic structures 214. The reservoirs 207 are placed on base plate 210. The pipetting unit 212 is operatively coupled to an automated positioning device (not shown) for transferring the pipetting tip 213 with respect to the reservoirs 207 and the chip 202. The microfluidic system 201 further includes a detecting unit 208 which detects particle-bound labeled analytes contained in the second retention zones 224 of the second reaction chambers 223. The detecting unit 208 may be, e.g., embodied as a fluorescence detector having a light source for the generation of light 209 that is emitted towards the second retention zones 224, and a fluorescence sensor for sensing the fluorescence light emitted from fluorescence markers made to be bound to particle-bound analytes when retained in the first reaction chambers 219.

The microfluidic system 201 yet further includes a controller which receives information from the different components of the system 201, and also generates and transmits corresponding control signals for controlling the components.

With particular reference to FIG. 7, in the microfluidic system 201, the platform 203 is provided with a plurality of first magnets 226. The first magnets 226 in one embodiment are arranged in a circumferential direction such that the first magnets 226 are positioned below the first reaction chambers 219 in correspondence to the first retention zones 220 in order to retain magnetically responsive particles within the first reaction chambers 219. In another embodiment, the platform 203 is further provided with a plurality of second magnets 227 which are arranged in a circumferential direction such that the second magnets 227 are positioned below the second reaction chambers 223 in correspondence to the second retention zones 224 in order to retain magnetically responsive particles within the second reaction chambers 223. In one embodiment, the second magnets 227 are arranged in a radial-outward position with respect to the first magnets 226.

The first and second magnets 226, 227, respectively, may be embodied, e.g., as permanent magnets or electromagnets. The first magnets 226 are adapted to generate magnetic fields which have sufficient magnetic strength, e.g. pull force, to attract the magnetically responsive particles contained in the first reaction chambers 219, to at least partially and to at least temporarily accumulate them at the first retention zones 220. The second magnets 227 are adapted to generate magnetic fields which have sufficient magnetic strength, e.g. pull force, to attract the magnetically responsive particles transferred to the second reaction chambers 223, to at least partially and to at least temporarily accumulate the particles at the second retention zones 224.

Since both the first and second magnets 226, 227 co-rotate with the chip 202, a constant magnetic field is applied on the magnetically responsive particles in the first and second reaction chambers 219, 223, respectively, as well as also during rotation of the chip 202.

With specific reference to FIG. 8 illustrating a flowchart, another embodiment of an exemplary method for the automated analysis of samples using the above described microfluidic system 201 depicted by FIG. 7 is explained.

I: The process starts.

II: Magnetically responsive particles are provided in the first reaction chamber 219. In on e embodiment, such particles are provided by using the pipetting tip 213 to transfer a suspension of magnetically responsive particles from one of the fluid reservoirs 207, which contains the suspension, to each of the particle inlet zones 217, followed by rotating the platform 203 with a predetermined rotational speed to transfer predetermined volumes of the suspension from the particle inlet zones 217 through the particle conduits 218 to the first reaction chambers 219 by means of a centrifugal force. In one embodiment, the magnetically responsive particles carry immobilized molecular binding elements which attach to an outer surface thereof and which can specifically bind to an analyte, and of which the presence and optionally the concentration of the analyte contained in the samples can be tested. In another embodiment, the analyte can attach to the outer surface of the magnetically responsive particles. When transferred to the first reaction chambers 219, the first magnets 226 magnetically attract the magnetically responsive particles at the first retention zones 220 in the first reaction chambers 219.

III: Samples are provided in the first reaction chambers 219 which contain an analyte that can specifically interact with and, e.g., can bind to the particles. In one embodiment, the samples are provided by using the pipetting tip 213, wherein the samples are transferred from another one of the reservoirs 207 which contains the samples to each of the sample inlet zones 215, followed by rotating the platform 203 with a predetermined rotational speed in order to transfer the samples from the sample inlet zones 215 into the first reaction chambers 219 by means of a centrifugal force. Efficient mixing in the first reaction chambers 219 enables the analyte contained therein to specifically bind to the molecular binding elements of the magnetically responsive particles, and which can be, e.g., achieved as above described in connection with process III of FIG. 5.

IV: Labeling of the particle-bound analytes retained in the first reaction chambers 119 is then performed. In one embodiment, the particle-bound analytes are labeled by use of the pipetting tip 213, wherein a fluid containing detectable molecular labels, such as fluorescence markers adapted to specifically bind to the analytes, in this case to the particle-bound analytes, is transferred from another one of the reservoirs 207 which contains the labels into each of the sample inlet zones 215 and/or the particle inlet zones 217 or another inlet zones (not shown). The transfer is then followed by rotating the platform 203 with a predetermined rotational speed in order to transfer the fluids from the sample inlet zones 215 towards the waste zones 221 passing through the first reaction chambers 219 and the second reaction chambers 223 by means of a centrifugal force. Supplying the label containing fluids to the first reaction chambers 219 and, e.g., repeating the mixing process as described above in process III enables the labels contained therein to specifically and efficiently bind to the particle-bound analytes.

V: Non-bound labels are removed. In one embodiment, the non-bound labels are removed by use of the pipetting tip 213, wherein a washing fluid is transferred from another one of the reservoirs 207 which contains the washing fluid to each of the sample inlet zones 215. This transfer is then followed by rotating the platform 203 with a predetermined rotational speed in order to transfer the washing fluid from the sample inlet zones 215 into the first reaction chambers by means of a centrifugal force, thereby enabling the fluid surrounding the magnetically responsive particles retained in the first retention zones 220 to be flushed away into the waste zones and to be replaced by the washing fluid, thus removing the non-bound labels. Such a washing may be repeated as often as necessary.

VI: Transfer of the magnetically responsive particle-bound analytes from the first reaction chambers 219 to the second reaction chambers 223 and accumulation of the particle-bound analytes in the second reaction chambers 223. In one embodiment, the platform 203 is rotated with a higher rotational speed than that used for transferring the particles from the particle inlet zones 217 to the first reaction chambers 219 in order to release the particles from the first reaction chambers 219 and to flush it into the second reaction chambers 223. In the second reaction chambers 223, the particle-bound analytes are then accumulated by the second magnets 227 in the second retention zones 224.

VII: The presence and optionally concentration of the analyte in the samples are determined. In one embodiment, the detect unit 208 measures an intensity of the labels, such as a fluorescence intensity of the labeled particle-bound analytes retained in the second retention zones 224 of the second reaction chambers 223, and based on the result obtained, the presence and optionally the concentration of the analyte contained in the samples is determined.

VIII: The process stops.

Figure 9:
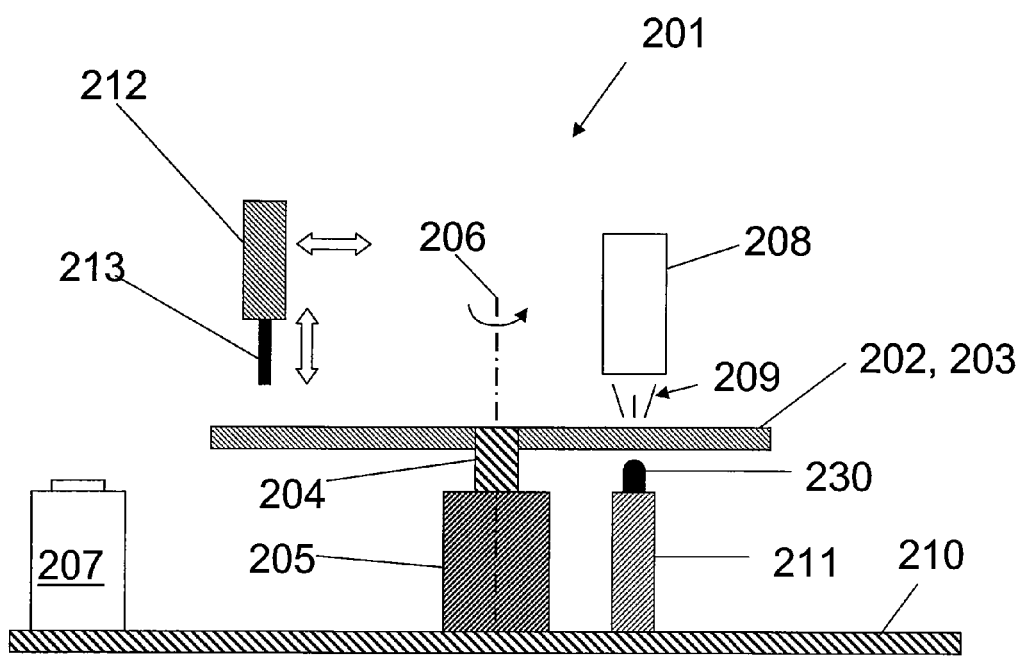
FIG. 9 depicts a schematic sectional view of a variant of the exemplary embodiment of the microfluidic system of FIG. 7.

With particular reference to FIG. 9, a variant of the centrifugal force based microfluidic system 201 of FIG. 7 is explained. In order to avoid unnecessary repetitions, only the differences with respect to the microfluidic system 201 of FIG. 7 are explained and otherwise reference is made to the description given in connection with FIGS. 6 to 8.

In this alternative embodiment of the microfluidic system 201, one or plural third magnets 230 are positioned on the base plate 210 and supported by a carrier 211 in correspondence to the second retention zones 224 of the second reaction chambers 223 in order to retain magnetically responsive particles within the second reaction chambers 223. In FIG. 9, only one single third magnet 230 is shown for the purpose of illustration only. The following explanations similarly apply to the case of a plurality of third magnets 230. The base plate-positioned third magnet 230 is arranged in a radial-outward position with respect to the first magnets 226 (FIG. 7) that is fixed to the platform 203. The third magnet 230 is adapted to generate a magnetic field which has sufficient magnetic strength, e.g. pull force, in order to attract the magnetically responsive particles contained in the second reaction chambers 223, and to at least partially and to at least temporarily accumulate them at the second retention zones 224.

Hence, in this variant, the first magnets 226 co-rotating with the turning chip 202 can exercise a constant magnetic field on the magnetically responsive particles in the first reaction chambers 219 also during rotation of the chip 202.

On the other hand, because the third magnet 230 does not co-rotate with the chip 202, the magnetic field applied on the magnetically responsive particles retained in the second retention zones 224 of the second reaction chambers 223 is not constant during rotation of the chip 202. In other words, the influence of the third magnet 230 on the magnetically responsive particles increases when the rotational speed of the chip 202 is decreased and vice versa. The third magnet 230 may have, e.g., a function to collect the magnetically responsive particles retained in the second retention zones 224 before detection.

Using the microfluidic system 201 of FIG. 9, in the above described method for the automated analysis of samples explained in connection with FIG. 8, in process VI, the accumulation of the labeled particle-bound analytes in the second retention zones 224 may be performed by rotating the platform 203 bi-directionally to perform a reciprocating rotary motion of the chip 202 with respect to the magnetic field of the base plate-fixed third magnet 230. For example, in one embodiment, amplitude of the reciprocating rotary motion can be decreased from a predetermined maximum amplitude to a predetermined minimum amplitude, e.g., zero in one embodiment, and about zero in another embodiment. In that, the reciprocating rotary motion of the chip 202 is operatively coupled to the magnetic field of the non-rotating third magnet 230 to locally accumulate (i.e. concentrate) the particles at individual second retention zones 224.

While not shown in FIG. 9, second magnets 227 as illustrated in FIG. 7 may be present together with the third magnet 230 fixed to the platform 203 as illustrated in FIG. 7.

Figure 10:
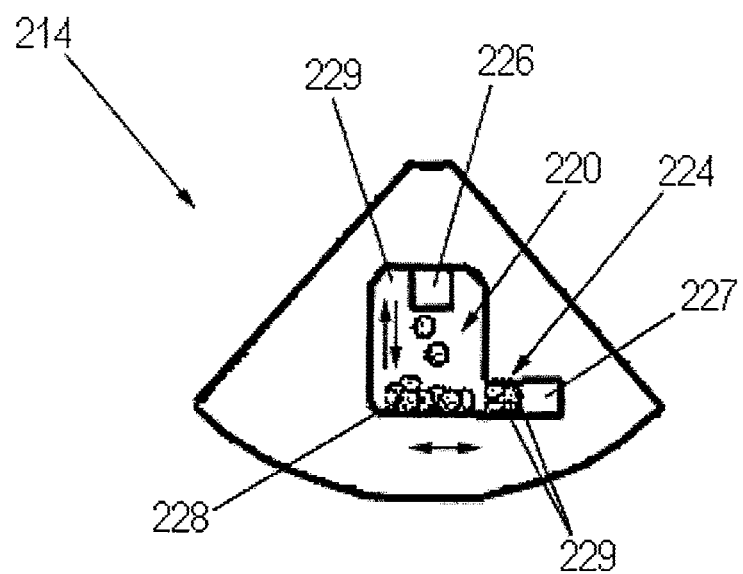
FIG. 10 depicts a schematic top view of another variant of the exemplary embodiment of the microfluidic system of FIG. 7.

With particular reference to FIG. 10, another variant of the centrifugal force based microfluidic system 201 of FIG. 7 is explained. In order to avoid unnecessary repetitions, only the differences with respect to the microfluidic system 201 of FIG. 7 are explained and otherwise reference is made to the description given in connection with FIGS. 6 to 8.

Accordingly, the chip 202 is provided with plural microfluidic structures 214, one of which is partially depicted in FIG. 10. The microfluidic structure 214 differs from the microfluidic structure of FIG. 6 in that it includes only one single reaction chamber 219 that is fluidically connected to a sample inlet zone (not shown) and a particle inlet zone (not shown) as well as a waste zone (not shown) by microcapillary fluid conduits as illustrated in FIG. 6.

The reaction chamber 219 of each of the microfluidic structures 214 comprises a first retention zone 220 and a second retention zone 224 separately arranged with respect to the first retention zone 220. The first retention zone 220 may be, e.g., used for mixing magnetically responsive particles 228, carrying molecular binding elements, with the samples that contain at least one analyte for binding to the molecular binding elements as well as labeling and washing the labeled particle-bound analytes. The second retention zone 224 may be used, e.g., for detection of labeled particle-bound analytes after they have been transferred from the first retention zone 220 to the second retention zone 224.

In the microfluidic system 201, in one embodiment, the platform 203 is provided with a plurality of first magnets 226 which are arranged in a circumferential direction such that the first magnets 226 are positioned below the reaction chambers 219 in correspondence to the first retention zones 220 in order to retain the magnetically responsive particles 228 within the first retention zones 220. In another embodiment, the platform 203 is further provided with a plurality of second magnets 227 which are arranged in a circumferential direction such that the second magnets 227 are positioned below the reaction chambers 219 in correspondence to the second retention zones 224 in order to retain the magnetically responsive particles 228 within the second retention zones 224. In one embodiment, the second magnets 227 are arranged in a radial-outward position with respect to the first magnets 226. The first magnets 226 are adapted to generate magnetic fields which have sufficient magnetic strength, e.g. pull force, in order to attract the magnetically responsive particles 228, and to at least partially and to at least temporarily accumulate them at the first retention zones 220. The second magnets 227 are adapted to generate magnetic fields which have sufficient magnetic strength, e.g. pull force, in order to attract the magnetically responsive particles 228, and to at least partially and to at least temporarily accumulate them at the second retention zones 224.

Since both the first and second magnets 226, 227 can co-rotate with the chip 202, a constant magnetic field is applied on the magnetically responsive particles 228 in the first and second retention zones 220, 224, respectively, as well as also during rotation of the chip 202. Otherwise, only the first magnets may co-rotate with the chip.

As illustrated in FIG. 10, in order to mix the magnetically responsive particles 228 with the analyte containing sample in the first retention zone 220 of the reaction chamber 219, the particles 228 can be moved back and forth in a radial direction when performing a rotational motion in which the platform 203 is alternatively rotated such that a centrifugal force is caused that is sufficient for outbalancing a magnetic force of the magnetic field of the first magnet 226 or in another embodiment, alternatively rotated such that a centrifugal force is caused that is outbalanced by the magnetic force of the magnetic field of the first magnet 226.

Otherwise, by suitably adjusting the rotational speed of the platform 203, the particles 228 may be retained at the second retention zone 224 that is provided with guiding faces 229, and in combination with the magnetic force of the second magnet 227, the particles 228 can be used to accumulate locally in the second retention zone 224. As illustrated, the guiding faces 229 may create as smaller compartment within the reaction chamber 219.

According to the various embodiments as-above explained, due to the fact that particle-bound analytes typically tend to re-arrange, such as caused by diffusion and/or flow-disturbances and/or relaxation effects when rotational movement of the platform 103, 203 is stopped, fixation of the labeled particle-bound analytes within the retention zone when detection is performed advantageously enhances the reliability of the measurement.

According to the various embodiments as-above explained, due to the fact that, e.g., stray light of fluorescence markers may be scattered from inner walls of the retention zones that contain the labeled particle-bound analytes, thereby reducing the reliability of the measurement, and/or due to the fact that fluorescence markers may also non-specifically bind to the inner walls of the retention zones, magnetic trapping of the labeled particle-bound analytes advantageously allows for positioning the particles to have greater distance from the inner walls of the retention zones to thereby advantageously enhance the reliability of the measurement.

Obviously many further modifications and variations of the present invention are possible in light of the above description. It is therefore to be understood, that within the scope of appended claims, the invention may be practiced otherwise than as specifically devised.

What is claimed is:

1. A centrifugal force based microfluidic system for the automated analysis of samples containing at least one analyte involving the use of magnetically responsive particles which interact with said analyte, said system comprising:
   at least one rotatable supporting device;
   at least one microfluidic device directly fixed to said supporting device so as to rotate therewith and provided with at least one microfluidic structure having at least one inlet zone, at least one reaction chamber which receives one of said samples and which is in fluid communication with said at least one inlet zone comprising at least a first retention zone and a second retention zone in fluid communication with said first retention zone which retain said magnetically responsive particles;
   at least one first magnet directly fixed to said supporting device in correspondence to said at least one first retention zone so as to rotate therewith and to generate a magnetic field which retains said magnetically responsive particles in said first retention zone; and
   at least one second magnet directly fixed to said supporting device in correspondence to said at least one second retention zone so as to rotate therewith and to generate another magnetic field which retains said magnetically responsive particles in said second retention zone.

2. The system according to claim 1, wherein said microfluidic device is provided with at least one recess which accommodates said at least one first magnet so as to reduce a distance between said first retention zone and said at least one first magnet.

3. The system according to claim 1, wherein said microfluidic device is provided with at least one recess which accommodates said at least one second magnet so as to reduce a distance between said second retention zone and said at least one second magnet.

4. The system according to claim 1, wherein said system further comprises
   at least one third magnet separated from said supporting device so that said supporting device rotates with respect to said at least one third magnet.

5. The system according to claim 4, wherein said microfluidic device is provided with at least one first recess which accommodates said at least one first magnet so as to reduce a distance between said at least one first magnet and said at least one first retention zone, and at least one second recess which accommodates said at least one second magnet so as to reduce a distance between said at least one second magnet and said at least one second retention zone.

6. The system according to claim 4, wherein said at least one second retention zone is provided with at least one guiding face which accumulates said magnetically responsive particles within said at least one second retention zone.

7. The system according to claim 1, wherein said microfluidic device is provided with at least one first recess which accommodates said at least one first magnet so as to reduce a distance between said at least one first magnet and said at least one first retention zone, and at least one second recess which accommodates said at least one second magnet so as to reduce a distance between said at least one second magnet and said at least one second retention zone.

8. The system according to claim 1, further comprising at least one magnetic flux concentrator which concentrates a magnetic flux of one said magnets so as to increase magnetic interaction with said magnetically responsive particles.

9. The system according to claim 1, wherein said at least one second retention zone is provided with at least one guiding face which accumulates said magnetically responsive particles within said at least one second retention zone.

10. The system according to claim 1, wherein said microfluidic structure has a first reaction chamber and a second reaction chamber, said first reaction chamber comprising said first retention zone and said second reaction chamber comprising said second retention zone.

11. The system according to claim 1, further comprising at least one waste zone which receives waste fluid and which is in fluid communication with said at least one reaction chamber.

12. The system according to claim 1, wherein said microfluidic device is removably fixed to said supporting device.

13. A centrifugal force based microfluidic system for the automated analysis of samples containing at least one analyte involving the use of magnetically responsive particles adapted to specifically interact with said analyte, comprising:
   at least one rotatable supporting device;
   at least one microfluidic device removably fixed to said supporting device so as to rotate therewith and provided with at least one microfluidic structure having at least one inlet zone, at least one reaction chamber for receiving one of said samples in fluid communication with said at least one inlet zone comprising at least a first retention zone and a second retention zone in fluid communication with said first retention zone adapted for the retention of said magnetically responsive particles;
   at least one first magnet directly fixed to said supporting device in correspondence to said first retention zone so as to rotate therewith for generating a magnetic field, and
   at least one second magnet directly fixed to said supporting device in correspondence to said second retention zone so as to rotate therewith for generating a magnetic field,
   wherein said at least one first magnet for generating a magnetic field acting on said magnetically responsive particles is configured to retain said magnetically responsive particles in said first retention zone and said at least one second magnet for generating a magnetic field acting on said magnetically responsive particles is configured to retain said magnetically responsive particles in said second retention zone.

14. The system according to claim 13, wherein said microfluidic device is provided with at least one recess adapted for accommodating said at least one first magnet so as to reduce a distance between said first retention zone and said at least one first magnet.

15. The system according to claim 13, wherein said microfluidic device is provided with at least one recess adapted for accommodating said at least one second magnet so as to reduce a distance between said second retention zone and said at least one second magnet.

16. The system according to claim 13, wherein said system further comprises
   at least one third magnet separated from said supporting device so that said supporting device can be rotated with respect to said at least one third magnet.

17. The system according to claim 13, wherein said microfluidic device is provided with at least one first recess adapted for accommodating said at least one first magnet so as to reduce a distance between said at least one first magnet and said at least one first retention zone and with at least one second recess adapted for accommodating said at least one second magnet so as to reduce a distance between said at least one second magnet and said at least one second retention zone.

18. The system according to claim 13, further comprising at least one magnetic flux concentrating means adapted for concentrating a magnetic flux of one said magnets so as to increase magnetic interaction with said magnetically responsive particles.

19. The system according to claim 13, wherein said second retention zone is provided with at least one guiding face adapted for accumulating said magnetically responsive particles within said at least one second retention zone.

20. The system according to claim 13, wherein said microfluidic structure has a first reaction chamber and a second reaction chamber, said first reaction chamber comprising said first retention zone and said second reaction chamber comprising said second retention zone.

* * * * *